(12) United States Patent
Sato et al.

(10) Patent No.: US 7,347,355 B2
(45) Date of Patent: Mar. 25, 2008

(54) METHOD FOR BRAZING METAL COMPONENTS FOR USE IN MEDICAL EQUIPMENT, METAL ASSEMBLY PRODUCED BY THE METHOD AND ENDOSCOPE PROVIDED WITH THE METAL ASSEMBLY

(75) Inventors: Yasuyuki Sato, Saitama (JP); Yoshihiro Obata, Saitama (JP); Wataru Murai, Miyagi (JP); Ryoji Tokieda, Saitama (JP); Naoki Kamiya, Saitama (JP); Hideo Shimizu, Saitama (JP)

(73) Assignees: PENTAX Corporation, Tokyo (JP); Shinwa Heat Treatment Co., Ltd., Saitama (JP)

( * ) Notice: Subject to any disclaimer, the term of this patent is extended or adjusted under 35 U.S.C. 154(b) by 195 days.

(21) Appl. No.: 10/922,953

(22) Filed: Aug. 23, 2004

(65) Prior Publication Data
US 2005/0077343 A1    Apr. 14, 2005

(30) Foreign Application Priority Data
Aug. 22, 2003 (JP) .............................. 2003-299055
Jul. 27, 2004 (JP) .............................. 2004-219270

(51) Int. Cl.
*B23K 31/02* (2006.01)

(52) U.S. Cl. .................. 228/220; 228/221; 228/256

(58) Field of Classification Search .................. None
See application file for complete search history.

(56) References Cited

U.S. PATENT DOCUMENTS 4,081,121 A *  3/1978  Picard ......................... 228/181
5,217,026 A *  6/1993  Stoy et al. ................... 600/585

(Continued)

FOREIGN PATENT DOCUMENTS

JP          63-130263          6/1988

(Continued)

OTHER PUBLICATIONS

"Selection and Using of Brazing-Filler", New Edition, Edited by Noble Metal Brazing Department of Japan, Sanpo Publication Co., Ltd., Jun. 20, 1990, pp. 32-35, with English language translation of the same.

(Continued)

*Primary Examiner*—Kiley Stoner
(74) *Attorney, Agent, or Firm*—Greenblum & Bernstein, P.L.C.

(57) ABSTRACT

A method for brazing two or more of stainless steel components for use in medical equipment, in which one component is joined to other component using a brazing material containing Au of which amount is 62.5 wt % or higher, the method comprising the steps of: a first step in which the components are subjected to a heat treatment at a temperature of 1,050 to 1,200° C. in a hydrogen containing atmosphere or in a vacuum; a second step in which one of the components is allowed to close to the other component so as to form a gap therebetween; and a third step in which the brazing material in a molten state is supplied into the gap to join the components together to manufacture a metal assembly. The joint portions formed in the metal assembly have excellent chemical resistance and corrosion resistance, and thus the metal assembly is suitably used in an endoscope.

13 Claims, 4 Drawing Sheets

U.S. PATENT DOCUMENTS 6,257,882 B1 * 7/2001 Wyllie, II ................ 433/8
2005/0116208 A1 * 6/2005 Watsuji ................ 252/512

FOREIGN PATENT DOCUMENTS

| JP | 7-79911 | 3/1995 |
| JP | 8-266462 | 10/1996 |
| JP | 10-96184 | 4/1998 |
| JP | 11-221668 | 8/1999 |
| JP | 2003-199706 | 7/2003 |
| JP | 2004-141184 | 5/2004 |
| JP | 2004141184 A * | 5/2004 |

OTHER PUBLICATIONS

"Welding and Joining Handbook", Edited by Japan Welding Society, Maruzsen Co., Ltd., Sep. 30, 1990, pp. 436-448, with English language translation of the same.

* cited by examiner

METHOD FOR BRAZING METAL COMPONENTS FOR USE IN MEDICAL EQUIPMENT, METAL ASSEMBLY PRODUCED BY THE METHOD AND ENDOSCOPE PROVIDED WITH THE METAL ASSEMBLY

BACKGROUND OF THE INVENTION

1. Field of the Invention

This invention relates to a method for brazing metal components for use in medical equipment, a metal assembly produced by the method and an endoscope provided with the metal assembly.

2. Description of the Prior Art

In medical equipment such as endoscopes, there is an apparatus of the type in which various instruments are to be inserted into the inside of a patient through the apparatus. Examples of such instruments include a monitoring scope which roles as a sensor for diagnosing the inside of a patient, a surgical knife for collecting a part of a body tissue, and an actuator for supplying a liquid for disinfecting or washing a part to be diagnosed or a gas such as air for locally blowing up the inside of a body cavity for making the diagnosis easy, and the like.

In general, such medical equipment is provided with a metal assembly so-called as a cylinder assembly through which various sensors and actuators are connected to tubes and wires and the like (see, for example, Japanese Laid-open Patent Application Publication No. 2003-199706).

In such a cylinder assembly, a cylinder body is brazed or joined with various pipe joints or the like which guide tubes and wires for connecting sensors and actuators which are to be placed inside the body cavity with operating sections used in the outside of the patient.

Conventionally, when the cylinder body is coupled with the pipe joints, openings are formed in the cylinder body, and then each pipe joint is inserted into the opening and then the joint portion is brazed together using various brazing filler metals.

In the meantime, recently, there are cases that resistant bacteria which cause hospital-in infection and deadly germs such as SARS are spread in hospitals. Therefore, there is a tendency that the medical equipment is disinfected or sterilized with a strong disinfectant containing peracetic acid and the like.

However, this in turn raises a problem in that the brazing portions (joint portions) in the conventional metal assemblies which were formed using various brazing filler metals are eroded with the strong disinfectant containing peracetic acid and the like, thus leading to a case that the function thereof is impaired.

SUMMARY OF THE PRESENT INVENTION

It is therefore an object of the present invention to provide a method for brazing metal components for use in medical equipment by which the metal components can be joined with high accuracy and high brazing strength, a metal assembly produced by the method and an endoscope provided with the metal assembly.

In order to achieve the object, the present invention is directed to a method for brazing two or more of metal components made of stainless steel for use in medical equipment, in which one component is joined to other component using a brazing material containing Au of which amount is 62.5 wt % or higher. The method comprises the steps of: a first step in which the components are subjected to a heat treatment at a temperature of 1,050 to 1,200° C. in a hydrogen containing atmosphere or in a vacuum; a second step in which one of the components is allowed to close to the other component so as to form a gap therebetween; and a third step in which the brazing material in a molten state is supplied into the gap to join the unit components together.

According to the present invention described above, it is possible to join the metal components for use in medical equipment together with high accuracy and high brazing strength.

In the method described above, it is preferred that in the first step a dew point of the hydrogen containing atmosphere is −60° C. or lower. This makes it possible to eliminate oxidized passive coating formed on the metal components reliably.

Further, in the method described above, it is preferred that in the second step the gap is formed by inserting a part of one component into the other component. This makes it possible to join the metal component more reliably. In this case, it is preferred that at least one of the metal components is a hollow member. Further, each of the components may be a hollow member having an internal cavity, in which by inserting a part of one component into the internal cavity of the other component to form the gap. Although the method of the present invention can be applied to a joint between hollow members, a joint between a hollow member and a solid member, and a joint between solid members, this method is preferably applied to a joint in which at least one of the metal components is a hollow member.

Furthermore, in the method described above, it is preferred that the average width of the gap formed in the second step is in the range of 0.02 to 0.25 mm. This makes it possible to supply the joint material into the gap more reliably and uniformly.

Moreover, in the method described above, it is also preferred that the method further comprises, prior to the third step, a step of temporarily fixing the components by welding a part of the one component to a part of the other component by means of a laser welding. This also makes it possible to supply the joint material into the gap more reliably and uniformly.

Moreover, in the method described above, it is also preferred that the method further comprises, prior to the third step, a step of applying the brazing material along an opening of the gap, in which in the third step the brazing material is molten by heating the brazing material thereby supplying the brazing material in a molten state into the gap. This also makes it possible to supply the joint material into the gap more reliably and uniformly.

Moreover, in the method described above, it is also preferred that in the third step the heating temperature is in the range of 1,050 to 1,200° C. This makes it possible to prevent the brazing material from being alloyed with the metal components. Further, it is also possible to enhance the wettability of the brazing material against the stainless steel.

Moreover, in the method described above, it is also preferred that the third step is performed in a hydrogen containing atmosphere or in a vacuum. This makes it possible to prevent the surfaces of the stainless steel metal components from being oxidized to thereby maintain the wettability of the brazing material against the stainless steel satisfactorily.

Moreover, in the method described above, it is also preferred that in a state that the metal components are allowed to close to each other so that a surface of one metal component faces a surface of the other metal component, the method further comprises a step of forming at least one protrusion on at least one of the surfaces of the metal components so as to protrudes toward the other surface. This makes it possible to temporarily fix the metal components to each other when the components are positioned.

In this case, it is preferred that the protrusion is formed by overlying welding. This makes it possible to form a protrusion having a desired height without welding to a jig used in the formation of the protrusion. Further, it is also preferred that the step for forming the protrusion is carried out prior to the first step. This makes it possible for the protrusion to be subjected to the heat treatment, so that it is possible to supply the brazing material into the gap more reliably and uniformly.

Moreover, in the method described above, it is preferred that the brazing material is at least one selected from the group containing pure gold, Au—Ni based alloys, Au—Cu based alloys and Au—Ag—Cu based alloys. Since the brazing material formed of these materials has excellent chemical resistance and corrosion resistance against a strong disinfectant containing peracetic acid and the like, these materials are preferably used in the present invention.

Another aspect of the present invention is directed to a metal assembly for use in medical equipment, wherein the metal assembly is manufactured by brazing metal components made of stainless steel by the method described above. According to the metal assembly described above, since the brazing material containing Au of 62.5 wt % or more has excellent chemical resistance and corrosion resistance against a strong disinfectant containing peracetic acid and the like, it is possible to prevent the joint portions in the assembly from being eroded by a chemical solution such as a disinfectant or the like. In this case, it is preferred that each of the metal components is a component for forming a channel of an endoscope. Since such a channel is liable to be affected by the chemical solution when the endoscope is sterilized and washed, the present invention can be preferably applied to a metal assembly and metal components used in such a channel.

Other aspect of the present invention is directed to an endoscope provided with the metal assembly as described above. According to this invention, it is possible to provide an endoscope having excellent durability.

These and other objects, structures and results of the present invention will be apparent more clearly when the following detailed description of the preferred embodiment and the practical examples is considered taken in conjunction with the appended drawings.

DETAILED DESCRIPTION OF THE PREFERRED EMBODIMENT

Figure 1:
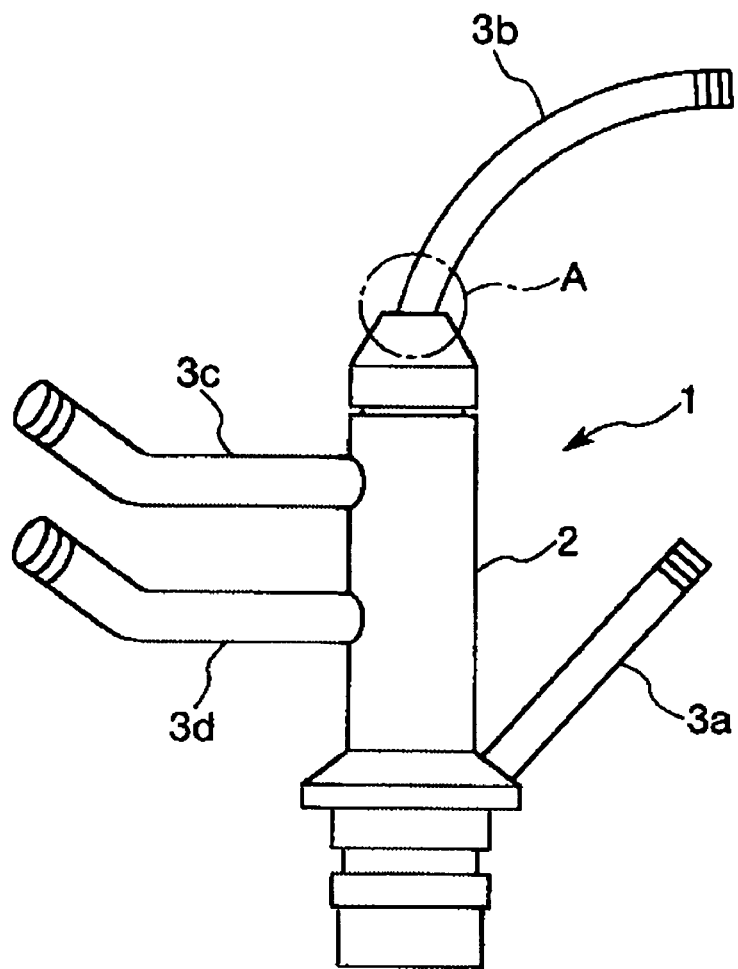
FIG. 1 is a perspective view which shows one example of a metal assembly for use in medical equipment according to the present invention.

Hereinbelow, a preferred embodiment of the present invention will be described with reference to the appended drawings.

In order to solve the problem described above, the inventors of the present invention have made extensive researches for brazing materials (brazing filler metals), and as a result, the inventors have reached a conclusion that as for a brazing material that is hard to be eroded by various disinfectants, a brazing material containing Au of which amount is 62.5 wt % (15K) or more (including pure gold) should be used.

However, such a brazing material has a poor wettability against a stainless steel. Therefore, when such a brazing material is used for brazing stainless steel components for use in medical equipment (hereinafter, these components are referred to as "metal components"), there is a case that a brazing material does not reach the entire of the brazing portion between the metal components. Further, since such a brazing material has high compatibility with stainless steel, it is easily alloyed with the stainless steel when a heat treatment is carried out at high temperature. Thus, depending on the kind of the metal components (for example, a pipe joint having an extremely thin wall thickness), deformation will occur due to erosion. In order to overcome these problems, it was necessary to carry out any pre-treatment on the metal components to be brazed or joined.

In view of this, the inventors have made further researches for other brazing methods for brazing the metal components using the brazing material. As a result, it has found that the wettabilty of the brazing material for the metal components (stainless steel components) is improved by performing in advance a heat treatment on the metal components to be joined in an hydrogen containing atmosphere or in a vacuum at a temperature of 1,050 to 1,200° C., so that the metal components can be brazed with high accuracy and high brazing strength.

Further, it has also found that when the brazing material is used, the metal components can be joined with higher accuracy and higher brazing strength by providing a joint gap (joint clearance) between the metal components to be joined though the size of the gap varies depending on the brazing method to be used or the size of the metal components to be joined.

The present invention was made in view of the above findings. Accordingly, the present invention is directed to a method for brazing two or more of stainless steel components for use in medical equipment, in which the metal components are joined to each other using a brazing material containing Au of which amount is 62.5 wt % or more, the method comprising the steps of: a first step in which the metal components are subjected to a heat treatment at a temperature of 1050 to 1200° C. in a hydrogen containing atmosphere or in a vacuum; a second step in which one of the metal components is allowed to close to the other metal component so as to form a gap therebetween; and a third step in which the brazing material in a molten state is supplied into the gap to join the metal components together.

The brazing material (brazing filler metal) to be used in the present invention contains Au of which amount is 62.5 wt % ore more. Examples of such a brazing material include a pure gold and Au based alloys such as Au—Ni based alloy which is comprised of Au of 81.5 to 82.5 wt %, other element of 0.15 wt % or less and Ni (balance), Au—Ag—Cu based alloy which is comprised of Au of 74.5 to 75.5 wt %, Ag of 12.0 to 13.0 wt %, other element of 0.15 wt % or less and Cu (balance), and Au—Cu based alloy which is comprised of Au of 79.5 to 80.5 wt %, other element of 0.15 wt % or less and Cu (balance). In the present invention, at least one of these materials can be preferably used.

Since all of these brazing materials have a high chemical resistance and corrosion resistance against a strong disinfectant containing peracetic acid and the like, they can be preferably used. In this connection, it is preferred that an Au alloy is used as a brazing material in the case where a high brazing strength is required at a brazing portion.

Further, the shape or form of the brazing material to be used is not particularly limited, and various shapes and forms may be used such as a wire form or a paste form containing powder of pure gold or Au alloy.

Hereinafter, with reference to FIG. 1 to FIG. 5, a method for brazing metal components according to the present invention will be described in details.

Figure 2:
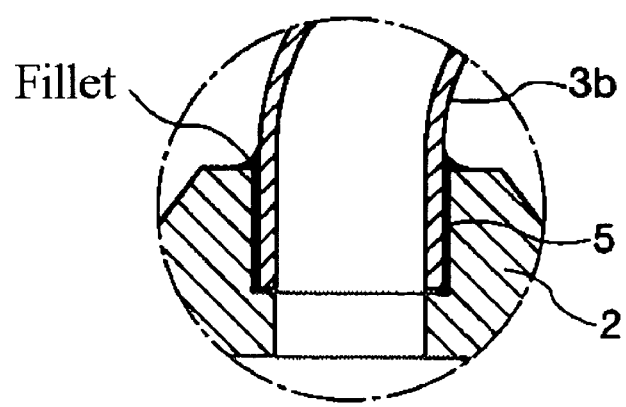
FIG. 2 is an enlarged cross-sectional view of a portion A indicated in FIG. 1.
Figure 3:
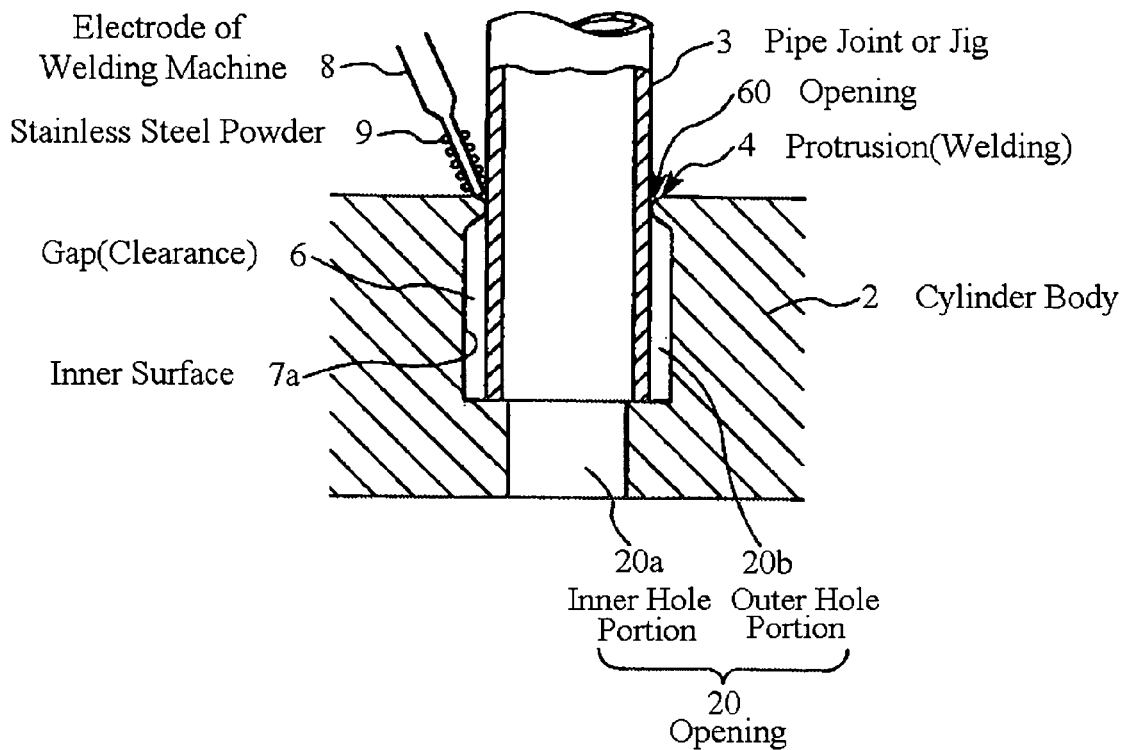
FIG. 3 is an illustration for explaining a method for forming a protrusion on the inner surface of a cylinder body by an overlaying welding method.
Figure 4:
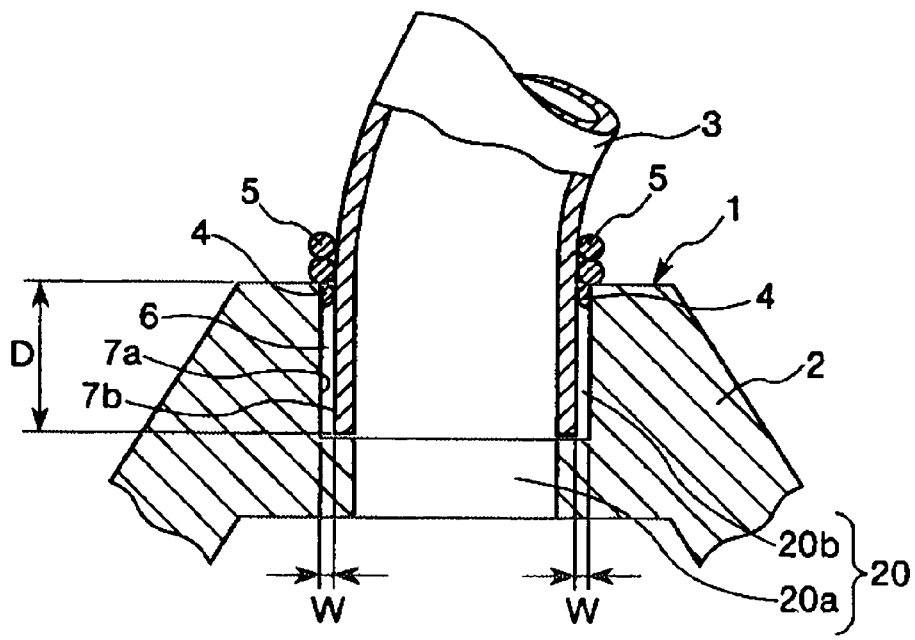
FIG. 4 is an illustration which shows one example of the method for brazing the metal components according to the present invention.
Figure 5:
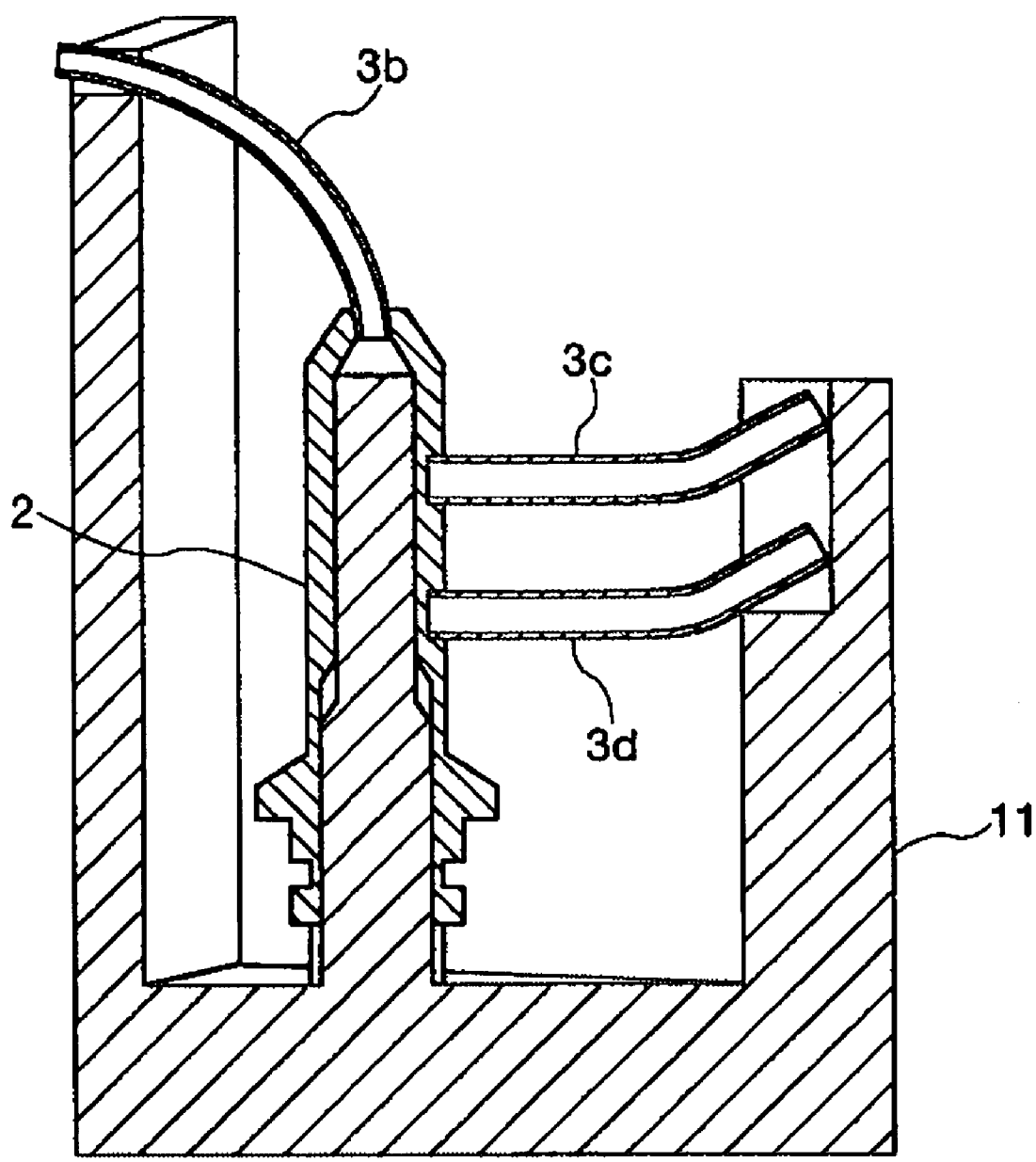
FIG. 5 is a cross-sectional view which shows a state that the cylinder body to which pipe joints are positioned is set in a welding positioner.

FIG. 1 is a perspective view which shows one example of metal components for use in medical equipment according to the present invention, FIG. 2 is an enlarged cross-sectional view of a portion A indicated in FIG. 1, FIG. 3 is an illustration for explaining a method for forming a protrusion on the inner surface of a cylinder body by an overlaying welding method, FIG. 4 is an illustration which shows one example of the method for brazing the metal components according to the present invention, and FIG. 5 is a cross-sectional view which shows a state that the cylinder body to which pipe joints are positioned is set in a welding positioner.

A metal assembly composed from the metal components for use in medical equipment 1 (hereinbelow, simply referred to as "metal assembly") shown in FIG. 1 is so-called as a guide cylinder (cylinder assembly), which comprises a cylinder body 2 and four pipe joints 3a to 3d joined to the cylinder body 2. The number of the pipe joints may be two, three or five or more, and the shape of the cylinder body 2 is not limited to one shown in the drawing and it may be changed depending on the kind and type of the medical equipment.

In the metal assembly 1, for example, the pipe joints 3a to 3d shown in FIGS. 1 and 2 constitute one metal component of the present invention (hereinbelow, these pipes will be collectively referred with the reference numeral 3) and the cylinder body 2 shown in FIGS. 1 and 2 constitutes the other metal component of the present invention.

The cylinder body 2 and the pipe joints 3 are formed of a stainless steel, and an austenitic stainless steel which has excellent chemical resistance (corrosion resistance) is preferably used. Examples of such austenitic stainless steel include SUS 304, 304L, 305, 316 and the like.

Further, the kinds of the stainless steels which constitute the cylinder body 2 and the pipe joints 3 (that is, the metal components to be joined) may be the same or different from each other. According to the brazing method of the present invention, it is possible to reliably join the metal components even in the case where these metal components are made of different stainless steels.

The cylinder body 2 has larger wall thickness and outer diameter as compared with those of each pipe joint 3. Further, in the cylinder body 2, there are formed openings 20 for receiving tip parts of the pipe joints 3, respectively.

On the other hand, in general, each of the pipe joints 3 has smaller wall thickness and outer diameter as compared with those of the cylinder body 2. These pipe joints 3 are joined with the cylinder body 2 by inserting a tip part of each pipe joint 3 into the opening 20 and then brazing it to the cylinder body 2 using a brazing material 5.

Further, as shown in FIG. 2 and FIG. 4, the openings 20 formed in the cylinder body 2 (the other metal component) are normally formed into stepped holes. Each of the stepped holes includes an inner hole portion 20a having a diameter which is the same as or substantially the same as the inner diameter of the pipe joint 3 and an outer hold portion 20b having a diameter which is slightly larger than the outer diameter of the pipe joint 3. For example, when the outer diameter of the pipe joint 3 is 5.5 mm, it is preferred that the outer hole portion 20b is formed so as to have a diameter of 5.52 to 5.58 mm.

<1> Protrusion Forming Step

First, on the inner surface 7a of the opening 20 (outer hole portion 20a) of the cylinder body 2, protrusions are formed as shown in FIGS. 3 and 4.

These protrusions 4 are provided for the purpose of reliably forming a joint gap (joint clearance) 6 between the cylinder body 2 and the pipe joint 3 for making the entry of the brazing material in a molten state easy at the subsequent step <5>, and for the purpose of temporarily fixing the pipe joint 3 with respect to the cylinder body 2 in a positioned state (which means not only a state where the pipe joint 3 can not be moved due to its own weight, but also a state where the pipe joint 3 can not be moved when the pipe joint 3 is set in a welding positioner 11 as described later).

In this connection, it is to be noted that in order to make the entry of the molten brazing material into the gap 6 easy, the gap 6 should preferably have the width of about 0.02 to 0.25 mm, and therefore, each of the protrusions should have the same height. Further, when the following conditions (i) to (iii) are satisfied, the number of the protrusions may be one which is in the form of a projection or convex portion. (i) the diameter of the opening (outer hole portion 20b) is smaller than 3 mm or less; (ii) the pipe joint 3 has a straight shape having no bent portions; and (iii) it is not necessary to carry out angular adjustment of the pipe joint 3 with respect to the cylinder body 2.

In this case (that is, only one protrusion 4 is formed), a part of the outer surface 7b of the pipe joint 3 is in contact with the inner surface 7a of the outer hole portion 20b of the cylinder body 2. However, the inventors have confirmed that the brazing material 5 can be also supplied to this contact portion sufficiently by appropriately setting the conditions in the subsequent steps <2> and <5>.

Further, in the case where the diameter of the opening 20 (the outer hold portion 20b) formed in the cylinder body 2 is larger than the above-mentioned value, or in the case where it is necessary to carry out angular adjustment of the pipe joint 3 with respect to the cylinder body 2, it is preferred that two or three or more (preferably three) protrusions 4 are formed. Further, in a specific case, such protrusions 4 may be formed by forming a plurality of notches in the inner circumferential portion of the opening through appropriate intervals.

In the case where a plurality of protrusions 4 are formed, it is preferred that these protrusions 4 have substantially the same size and that they are arranged through substantially the same interval (e.g. in the case of two protrusions, they are arranged through 180° interval, in the case of three protrusions, they are arranged through 120° interval, and in the case of four protrusions, they are arranged through 90° interval). According to these arrangements of the protrusions 4, the width of the joint gap 6 can be made equal along the circumferential direction of the pipe joint 3. As a result, it is possible to prevent the brazing material 5 in a molten state from flowing out outside the gap 6 and then entering other portions (such as an inner surface of the pipe joint 3 or an inner surface of the cinder body 2) so that a coating made of the brazing material 5 be formed at these portions due to uneven width of the gap.

Further, in this case, it is also preferred that each protrusion has such a size that the pipe joint 3 can be inserted into the outer hold portion 20b of the cylinder body 2 easily but difficult to be removed therfrom, and that the angular adjustment of the pipe joint 3 can be made easily.

A method for forming the protrusions 4 is not limited to a specific method, and various methods can be employed, but a method employing overlying welding is particularly preferred. In the case where the overlying welding method is employed, the protrusions 4 can be formed in accordance with the following manners. First, stainless steel powder is attached to a positive electrode of micro resistance welding or a stainless steel thin wire (e.g. having a diameter of 0.1 mm) is arranged in the vicinity of a positive electrode of micro TIG welding or micro MIG welding, and then the cylinder body 2 is connected to a negative electrode thereof. In this state, the positive electrode is made contact with or close to the inner surface 7a (including an edge of the outer hole portion 20b) of the outer hole portion 20b of the opening 20 formed in the cylinder body 2.

The overlying welding described above is carried out in a state that the pipe joint 3 or a jig having the same diameter as that of the pipe joint 3 is inserted into the outer hole portion 20b formed in the cylinder body 2. According to the overlying welding, protrusions 4 each having a desired height can be formed on the inner surface 7a without welding to the pipe joint 3 or the jig, and this is a merit of the use of the overlying welding method.

Besides the overlying welding method, the protrusions 4 may be formed by a deformation processing using a punch having guide portions of which diameter is substantially the same as that of the pipe joint 3 (caulking). This method using the punch is particularly useful when a plurality of protrusions 4 having substantially the same size and substantially the same interval are to be formed.

Further, by carrying out this step <1> prior to the subsequent step <2> (heat treatment step), it is possible for the protrusions 4 to be subjected to a heat treatment, so that the brazing material 5 can be supplied to the gap 6 (joint portion) reliably and uniformly.

The protrusions 4 may be formed on the outer surface 7b (joint surface) of the pipe joint 3 instead of forming them on the inner surface of the outer hole portion 20b of the cylinder body 2 as described above. Further, it is also possible to form the protrusions on both the outer surface 7b of the pipe joint 3 and the inner surface of the outer hole portion 20b.

<2> Heat Treatment Step (first step)

Next, the cylinder body 2 and the pipe joints 3 are subjected to a heat treatment in a hydrogen containing atmosphere containing hydrogen (namely, in an atmosphere containing hydrogen and being nonoxidized) or in a vacuum at a temperature of 1,050 to 1,200° C. (preferably, 1,080 to 1,150° C.).

By carrying out the heat treatment in this atmosphere, it is possible to reduce and eliminate oxidized passive coatings which are liable to be formed on the cylinder body 2 and the pipe joints 3. Further, it is also possible to cleanup the foreign substances attached to the surfaces of the cylinder body 2 and the pipe joints 3 (the foreign substances are eliminated by the reduction or vaporization thereof). As a result, the wettability and the adhesion of the brazing material 5 to the cylinder body 2 and the pipe joints 3 can be enhanced.

If this heat treatment is not carried out, the wettability of the brazing material to the cylinder body 2 and the pipe joints 3 are not enhanced, so that a sufficient amount of the brazing material can not be supplied to the gap (joint portion) 6 between the cylinder body 2 and each pipe joint 3. This will case such problems that a proper fillet cannot be formed, and that the brazing material in a molten state remains at a certain portion for a long time to be alloyed with the stainless steel which is a constituent material of the pipe joint 3 so that the wall thickness of the pipe joint 3 is locally reduced or the inner diameter of the pipe joint 3 is changed, thus resulting in impairing the functions of the pipe joint 3.

Further, the reason why the heat treatment is carried out at a temperature of 1,050° C. or higher is that, if the heating temperature is lower than 1,050° C., the reduction of the oxidized passive coatings becomes insufficient and therefore the wettability and adhesion of the brazing material to the stainless steel can not be sufficiently enhanced. On the other hand, the reason why the heat treatment is carried out at a temperature of 1,200° C. or lower is that even if the temperature is raised more than 1,200° C., the function and effect by the cleaning-up and reduction are saturated, and thus it is not expected that the effects described above are further enhanced. Further, if the temperature is too high, a crystalline grain size becomes coarse in the stainless steel, thus leading to problems in that the mechanical properties of the metal components which are subjected to a heat treatment are liable to be deteriorated, a cost for the heat treatment is increased, and the metal components which are subjected to the heat treatment are likely to be deformed, and the like.

A time for the heat treatment is not particularly limited, but it is preferably in the range of 1 to 60 min and more preferably in the range of 10 to 45 min.

When the heating treatment is carried out in a hydrogen containing atmosphere, it is preferred that a dew point of the hydrogen containing atmosphere is −60° C. or lower. The fact that a dew point of the hydrogen containing atmosphere is higher than −60° C. means that a hydrogen concentration in the hydrogen containing atmosphere is relatively low, and such a hydrogen containing atmosphere involves a poor reduction ability and thus there is a fear that the oxidized passive coatings cannot be eliminated sufficiently depending on the heating temperature. In this connection, it is to be noted that if the heating temperature is raised so as to be able to sufficiently eliminate the oxidized passive coatings by enhancing the reduction ability and the like, this in turn gives rise to an adverse effect on the metal components to be treated. Further, it is not preferable to prolong the heating time since this is not advantageous from an economic viewpoint.

Further, when the heating treatment is carried out in a vacuum (under reduced pressure), it is preferred that the degree of vacuum is $5 \times 10^{-4}$ mmHg or lower, and more preferably $5 \times 10^{-5}$ mmHg or lower. By setting the degree of vacuum to the above range, the elimination of the oxidized passive coatings and the cleaning-up of the foreign substances attached to the surfaces (that is, the foreign substances are eliminated by the reduction or vaporization thereof) can be made more reliably.

<3> Gap Formation Step (Positioning step: Second step)

Next, the pipe joint 3 is allowed to close to the cylinder body 2 so as to form a joint gap (joint clearance) 6 therebetween. In this embodiment, by inserting a tip part of the pipe joint 3 into the opening 20 (outer hole portion 20b) of the cylinder body 2, the gap 6 is formed therebetween.

In this regard, it is preferred that the width of the gap which is indicated by "W" in FIG. 4 is in the range of 0.02 to 0.25 mm in average. In particular, in the case where the outer diameter of the pipe joint 3 is 10 mm or less, it is preferred that the width W is in the range of 0.02 to 0.08 mm. Further, in the case where the outer diameter of the pipe joint 3 exceeds 10 mm but less than 30 mm, it is preferred that the width W is in the range of 0.032 to 0.089 mm. By setting the width of the gap 6 within the above range, it becomes possible to supply the brazing material 5 into the gap 6 reliably and uniformly in the following step <5>.

Further, it is preferred that the insertion depth of the pipe joint 3 (that is, the depth of the gap 6) which is indicated by "D" in FIG. 4 is 3.8 mm or less, and more preferably 3.5 mm or less. By setting the depth of the gap within the above range, it is possible to supply the brazing material 5 into the gap 6 more reliably and uniformly. As a result, the cylinder body 2 and the pipe joint 3 can be brazed or joined through a higher brazing strength.

In this embodiment, the protrusions are formed on the inner surface 7a of the outer hole portion 20b of the cylinder body 2 in the step <1>. Therefore, in this step <3>, the pipe joint 3 is temporarily fixed (positioned) with respect to the cylinder body 2 in a securely fitted state. This makes it possible to perform the operations in the steps following the step <4> more easily and reliably.

In this connection, it is to be noted that the above described step <1> (protrusion forming step) may be carried out subsequent to this step <3> (positioning step) without carrying out prior to the step <2>, or may be carried out twice, that is, prior to the step <2> and subsequent to the step <3>.

Alternatively, instead of performing the step <1> (protrusion forming step), it is possible to perform, subsequent to this step <3> (positioning step), a step for temporarily fixing the pipe joint 3 to the cylinder body 2 by welding a part of the pipe joint 3 to the cylinder body 2 using a laser welding. This provisionally fixing step by a laser welding may be carried out in addition to the step <1>.

According to this method in which the pipe joint 3 is temporarily fixed with respect to the cylinder body 2 using the laser welding, it is not necessary to deform the pipe joint 3 as is done in the case where the pipe joint 3 is forcedly inserted into the opening 20, and thus it is possible to prevent the function of the produced metal assembly 1 (that is, an unit composed from metal components for use in medical equipment) from being lowered. Further, since it is possible to form a gap properly, the brazing material is supplied into the gap reliably, thereby enabling to prevent lowering of the brazing strength.

Further, by using such a temporarily fixing method, it is possible to prevent the smoothness of the inner surface of the pipe joint 3 from being impaired, and as a result it is possible to prevent the functions of the pipe joints 3 (that is, the functions of the metal assembly 1) from being impaired.

For the reasons stated in the above, the method for brazing metal components according to the present invention is preferably applied to a case where at least one of metal components to be joined is a hollow member like the pipe joint 3 of this embodiment.

In this regard, it goes without saying that in the present invention both metal components to be joined are solid members.

<4> Brazing Material Applying Step

Next, a brazing material 5 which is not molten is applied along the circumferential opening 60 of the gap 6.

The application of the brazing material may be done by winding a brazing material 5 in the form of a filler wire (welding wire) around the circumference of the pipe joint 3 at the junction between the cylinder body 2 and the pipe joint 3 as shown in FIG. 4, or by applying a brazing material in a paste state around the junction. In this regard, it is to be noted that an amount of the brazing material to be applied is determined based on an amount necessary for brazing or joining the pipe joint 3 to the cylinder body 2.

In this case, it is preferred that the applied brazing material 5 is fixed with an adhesive (instant adhesive).

By applying the brazing material 5 into the gap 6 in this way, it is possible to supply the brazing material 5 into the gap 6 more reliably and uniformly.

<5> Brazing Step (Third step)

Next, as shown in FIG. 5, the cylinder body 2 to which the pipe joints 3 are positioned is set on a welding positioner 11. In this state, the brazing material 5 is heated and molten, and then the brazing material 5 in a molten state is supplied to each of the gaps 6. Thereafter, by hardening the brazing material 5 in a molten state, the cylinder body 2 and the pipe joints 3 are joined together.

The heating temperature for the brazing material 5 slightly varies depending on the kind of the brazing material 5 to be used and is not particularly limited to a specific temperature, but it is preferably in the range of 1,050 to 1,200° C., and more preferably in the range of 1,080 to 1,150° C. If the heating temperature is too low, the wettability of the brazing material against the stainless steel is not sufficiently enhanced, and as a result there is a fear that the brazing material 6 cannot be supplied into each gap efficiently. On the other hand, if the heating temperature is too high, a part of the brazing material 5 is consumed while the brazing material 5 is alloyed with the cylinder body 2 and the pipe joints 3 (base material), and as a result there is a fear that a role as the brazing material cannot be sufficiently performed. Further, there is a fear that a crystalline grain size becomes coarse in the stainless steel, thus leasing to the cases that mechanical properties of the metal components which are subjected to the heat treatment are deteriorated and that the pipe joints 3 are eroded.

A time for heating the brazing material 5 (that is, heating time) is also not particularly limited to a specific time, but it is preferably in the range of 1 to 60 min and more preferably in the range of 10 to 45 min.

Further, it is preferred that the brazing material 5 is heated in a hydrogen containing atmosphere containing hydrogen (namely, in an atmosphere containing hydrogen and being nonoxidized) or in a vacuum (under reduce pressure). This makes it possible to prevent the surfaces of the cylinder body 2 and the pipe joints 3 which are made of stainless steel from being oxidized, thereby enabling to maintain the wettability of the brazing material 5 for the stainless steel satisfactorily.

In the case where the brazing material 5 is heated in the hydrogen containing atmosphere, it is preferred that that a dew point of the hydrogen containing atmosphere is −60° C. or lower. The fact that a dew point of the hydrogen containing atmosphere is higher than −60° C. means that a hydrogen concentration in the hydrogen containing atmosphere is relatively low. In such a hydrogen containing atmosphere, there is a fear that the wettability of the brazing material 5 for the stainless steel can not be satisfactorily maintained depending of the kind of the brazing material to be used and the like.

On the other hand, in the case where the brazing material 5 is heated in a vacuum (under reduced pressure), it is preferred that the degree of vacuum is $5 \times 10^{-4}$ mmHg or lower, and more preferably $5\times10^{-5}$ mmHg or lower. By setting the degree of vacuum to the above range, it is possible to maintain the wettability for the stainless steel more reliably and satisfactorily.

Through the above steps, it is possible to obtain a metal assembly 1 (a unit composed from metal components for use in medical equipment) in which the cylinder body 2 is brazed or joined with the pipe joints 3.

Figure 6:
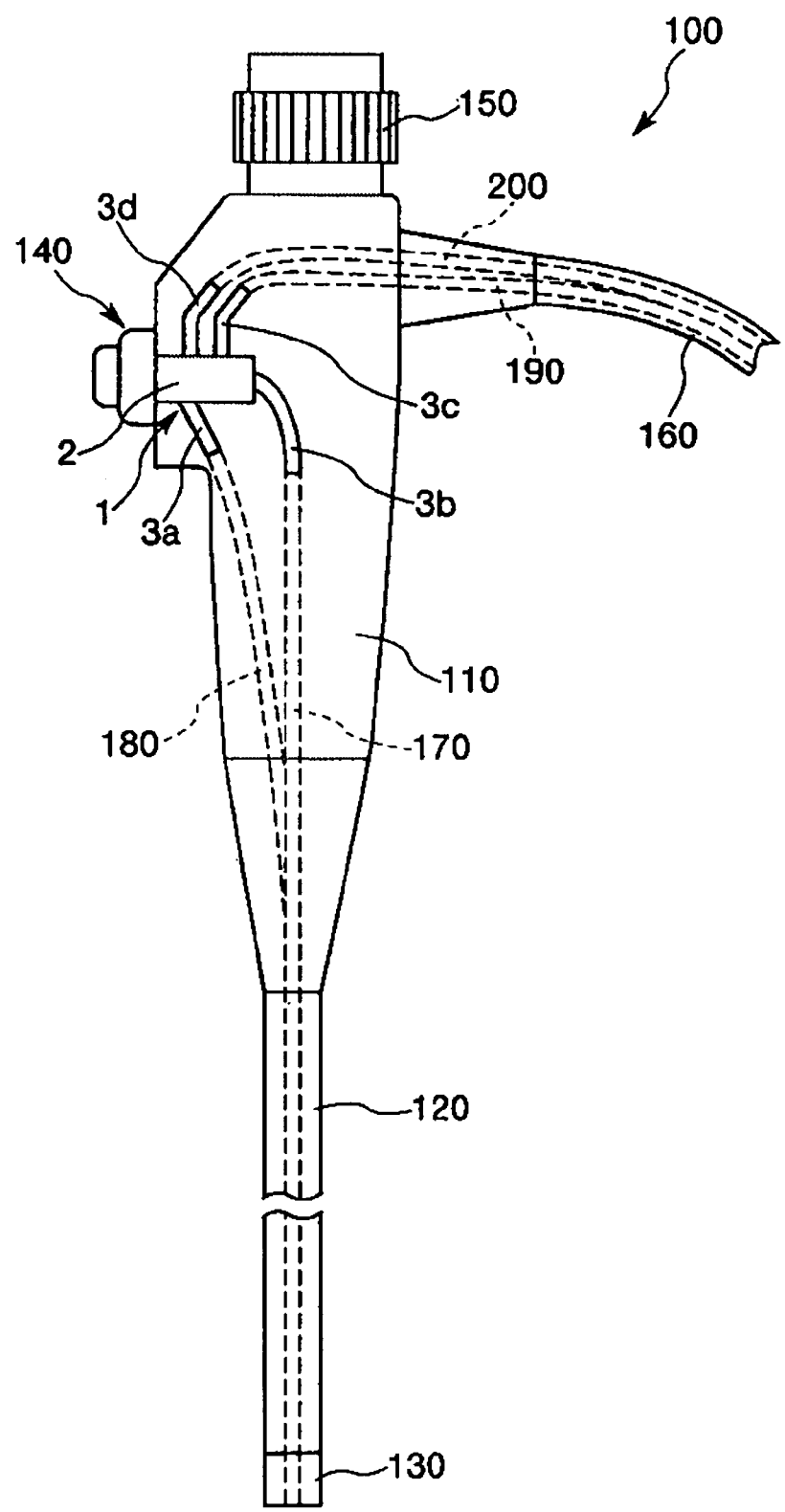
FIG. 6 is a plan view which shows one example of an endoscope according to the present invention.

By using such a metal assembly, it is possible to construct air feeding/water supplying button of an endoscope as shown in FIG. 6.

Hereinafter, a description will be made with regard to an endoscope according to the present invention. FIG. 6 is a plan view which shows an embodiment of an endoscope according to the present invention.

The endoscope 100 shown in FIG. 6 is used for diagnosing or examining stomach and other digestive tracts, and it is composed from an operating section 110 and a flexible insertion tube 120.

At the tip part of the flexible insertion tube 120, there is provided a tip part section 130 in which objective lenses and the like are housed.

On the operating section 110, there is provided an eye piece portion 150 at the upper portion thereof in addition to the air feeding/water supplying button 140 described above.

Further, a connecting flexible tube 160 is connected at one end thereof to the operating section 110, and a connector (not shown in the drawing) which is removably connected to a light source apparatus is provided at the other end of the connecting flexible tube 160.

Inside the operating section 110 and the flexible insertion tube 120, an air feeding channel 170 and a water supplying channel 180 extend therethrough, and these channels have openings at the tip part section 130.

The end portions of the air feeding channel 170 and water supplying channel 180 are directly connected to the pipe joint 3b and the pipe joint 3a of the guide cylinder 1 for the air feeding/water supplying button 140, respectively.

Further, an air feeding tube 190 and a water supplying tube 190 which are respectively connected to an external air feeding device and an external water supplying device (not shown in the drawing) extend inside the connecting flexible tube 16, and they are connected to a pipe joint 3c and a pipe joint 3d arranged on the side surface of the guide cylinder 1 for the air feeding/water supplying button 140, respectively.

When the endoscope 100 is sterilized or disinfected, chemicals or disinfectants are supplied into the inside the guide cylinder 1 (that is, the metal assembly of the present invention) of the air feeding/water supplying button 140. However, in the present invention, the cylinder body 2 and the pipe joints 3 are brazed or joined together using the brazing material 5 having excellent chemical resistance for the disinfectants or the like, and they are joined firmly using a sufficient amount of the brazing material 5. Therefore, it is possible to reliably prevent the chemicals from being leaked out from the joint portions of the guide cylinder 1 into the inside of the endoscope 100 even if the endoscope 100 is repeatedly sterilized and disinfected. With this result, it becomes possible to prevent internal devices or mechanisms of the endoscope 100 from being damaged and to prevent an increased force from being required upon bending the flexible insertion tube 120 (that is, a force required for the bending operation is not increased). In other words, it becomes possible to provide an endoscope 100 having excellent durability.

In the foregoing, the method for brazing the metal components for use in medical equipment, the metal assembly produced by the method and the endoscope provided with the metal assembly according to the present invention were described with reference to the embodiment shown in the drawings. However, the present invention is not limited to those described above.

For example, in the method for brazing the metal components of the present invention, other steps may be added for arbitral purposes.

Further, the method for brazing the metal components of the present invention is not limited to the embodiment described above where the method is applied to a case that the cylinder body 2 and the pipe joints 3 which constitute channel parts for the endoscope are to be joined together. For example, the method of the present invention may be applied to other case where channel parts of the endoscope which constitute instrument insertion channels are to be joined together.

Furthermore, the method of the present invention may be also applied to yet other cases in addition to the cases described above. Examples of such yet other cases include a case where a metal component which constitutes an endoscope is to be joined with other similar metal component, a case where a metal component which constitutes one of surgical instruments such as a forceps, a brush for diagnosing tissues or a puncture needle is to be joined with other similar metal component, a case where metal components which constitute internal parts of an endoscope such as an air feeding/water supplying bottle, various adapters (e.g. an adapter for photographing, an adapter for washing, an adapter for sterilization, an adapter for disinfection, and a three way stop cock), and a sliding tube for insertion are to be joined with other similar metal components.

As described above, the method of the present invention can be used for brazing various metal components with other metal components for use in medical equipment.

PRACTICAL EXAMPLES

Hereinbelow, practical examples of the present invention will be described.

A. Evaluation for the Brazing Conditions

Example 1A

First, a cylinder body and four pipe joints as shown in FIG. 1 were prepared.

The cylinder body was made of SUS 304, and the outer diameter, the wall thickness and the length thereof were 9 mm, 1.5 mm and 35 mm, respectively. Further, the pipe joints were also made of SUS 304, and the outer diameters thereof were in the range of 1.5 to 3.0 mm and the wall thickness of each pipe was 0.2 mm.

Next, openings in the forms of stepped holes corresponding to the respective pipe joints were formed in the cylinder body. Thereafter, the pipe joints were inserted into the corresponding openings, respectively. In this state, the cylinder body was connected to a negative electrode of a micro resistance joining machine, and stainless steel powder was attached to a positive electrode of the micro resistance joining machine as shown in FIG. 3, and then by operating the machine, one to three protrusions were formed on the inner surfaces of the openings, respectively.

Next, the four pipe joints were removed from the openings of the cylinder body. Thereafter, these metal components including the cylinder body and the pipe joints were placed in a continuous furnace and then subjected to a heat treatment under the pure hydrogen atmosphere (the dew point of hydrogen was $-73°$ C.). The heat treatment was being carried out at a temperature of $1,130°$ C. for 20 minutes (a warm-up period was 20 minutes and a cool-down period was 20 minutes).

Next, the four pipe joints were respectively inserted into the corresponding openings of the cylinder body again. At this time, the gap between the cylinder body and each of the pipe joints was 0.05 mm, and the insertion depth of each pipe joint was 3.5 mm.

Next, as shown in FIG. 4, a brazing material made of Au alloy composed of 82 wt % of Au and 18 wt % of Ni in the form of a filler wire (welding wire) having the diameter of 0.4 mm was wound around the outer circumference of each pipe joint for one or two turns, and then it was fixed using an instant adhesive.

Next, as shown in FIG. 5, a metal assembly composed from the cylinder body and the pipe joints positioned on the cylinder body was set in a welding positioner. Thereafter, the positioner with the metal assembly was placed in the continuous furnace having the pure hydrogen atmosphere (the dew point of hydrogen was −73° C.) which was also used in the previous heat treatment, and then the assembly was heated for brazing. The heating was being carried out at a temperature of 1,130° C. for 20 minutes (a warm-up period was 20 minutes and a cool-down period was 20 minutes), so that the respective pipe joints were brazed or joined with the cylinder body through the brazing material.

A guide cylinder was manufactured from the assembly produced in the manners described above.

Example 2A

A guide cylinder was manufactured in the same manner as in Example 1A excepting that the heat treatment was being carried out in a vacuum furnace having the degree of vacuum of 1×10⁻⁴ mmHg at a temperature of 1,130° C. for 20 minutes (a warm-up period was 20 minutes and a cool-down period was 20 minutes).

Example 3A

A guide cylinder was manufactured in the same manner as in Example 1A excepting that the brazing was being carried out in a vacuum furnace having the degree of vacuum of 1×10⁻⁴ mmHg at a temperature of 1,130° C. for 20 minutes (a warm-up period was 20 minutes and a cool-down period was 20 minutes).

Example 4A

A guide cylinder was manufactured in the same manner as in Example 1A excepting that the brazing was being carried out in an atmospheric furnace at a temperature of 1,130° C. for 20 minutes (a warm-up period was 20 minutes and a cool-down period was 20 minutes).

Example 5A

A guide cylinder was manufactured in the same manner as in Example 1A excepting that as the brazing material an Au alloy composed of 82 wt % of Au and 18 wt % of Cu in the form of a filler wire (welding wire) having the diameter of 0.4 mm was used.

Example 6A

A guide cylinder was manufactured in the same manner as in Example 1A excepting that as the brazing material a pure gold in the form of a filler wire (welding wire) having the diameter of 0.4 mm was used.

Example 7A

First, a cylinder body and two pipe joints were prepared.

The cylinder body was made of SUS 304, and the outer diameter, the wall thickness and the length thereof were 10 mm, 1.5 mm and 23 mm, respectively. Further, the pipe joints were also made of SUS 304, and the outer diameters and the wall thickness thereof were 4.0 mm and 0.2 mm, respectively.

Next, openings in the form of a stepped hole corresponding to the respective pipe joints were formed in the cylinder body. Thereafter, the pipe joints were inserted into the corresponding openings, respectively. In this state, the cylinder body was connected to a negative electrode of a micro resistance joining machine, and stainless steel powder was attached to a positive electrode of the micro resistance joining machine as shown in FIG. 3, and then by operating the machine, numbers of protrusions were formed on the inner surfaces of the openings intermittently along the circumference thereof (about ¾ of the circumference).

Next, the two pipe joints were removed from the openings of the cylinder body. Thereafter, these metal components including the cylinder body and the pipe joints were placed in a continuous furnace and then subjected to a heat treatment under the pure hydrogen atmosphere (the dew point of hydrogen was −76° C.). The heat treatment was being carried out at a temperature of 1,130° C. for 20 minutes (a warm-up period was 20 minutes and a cool-down period was 20 minutes).

Next, the two pipe joints were respectively inserted into the corresponding openings of the cylinder body again. At this time, the gap between the cylinder body and each of the pipe joints was 0.05 mm, and the insertion depth of each pipe joint was 3.5 mm.

Next, as shown in FIG. 4, a brazing material made of Au alloy composed of 75 wt % of Au, 12.5 wt % of Ag and 12.5 wt % of Cu in the form of a filler wire (welding wire) having the diameter of 0.4 mm was wound around the outer circumference of each pipe joint for two turns, and then it was fixed using an instant adhesive.

Next, as shown in FIG. 5, a metal assembly composed from the cylinder body and the pipe joints positioned on the cylinder body was set in a welding positioner. Thereafter, the positioner with the metal assembly was placed in the continuous furnace having the pure hydrogen atmosphere (the dew point of hydrogen was −76° C.) which was also used in the previous heat treatment, and then the assembly was heated for brazing. The heating was being carried out at a temperature of 1,130° C. for 20 minutes (the warm-up period was 20 minutes and the cool-down period was 20 minutes), so that the respective pipe joints were brazed or joined with the cylinder body through the brazing material.

A guide cylinder was manufactured from the assembly produced in the manners described above.

Comparative Example 1A

A guide cylinder was manufactured in the same manner as in Example 1A excepting that the heat treatment was omitted.

Comparative Example 2A

A guide cylinder was manufactured in the same manner as in Example 1A excepting that the temperature at the heat treatment was 1,000° C.

Comparative Example 3A

A guide cylinder was manufactured in the same manner as in Example 1A excepting that the temperature at the heat treatment was 1,250° C.

Comparative Example 4A

A guide cylinder was manufactured in the same manner as in Example 1A excepting that the heat treatment was carried out under the atmospheric condition.

Comparative Example 5A

A guide cylinder was manufactured in the same manner as in Example 7A excepting that the heat treatment was omitted.

For each of the guide cylinders manufactured in Examples 1A to 7A and Comparative Examples 1A to 5A, observation was carried out for the brazing strength at the joint portion and the longitudinal cross section at the joint portion.

As a result, in each of Examples 1A to 7A, it has been confirmed that a sufficient brazing strength was obtained at the joint portion thereof and that the gap was filled with the brazing material without formation of void.

On the other hand, in each of Comparative Examples, it has been confirmed that a sufficient brazing strength could not be obtained at the joint portion thereof and that there was a portion which had not been not filled with the brazing material at the joint portion thereof. In particular, in Comparative Example 3A, deformation was observed at a part of the pipe joint.

B. Evaluation for Durability (Chemical resistance)

Two endoscopes were manufactured in each of the following Examples and Comparative Examples.

Examples 1B to 7B

In each of Examples 1B to 7B, two guide cylinders were manufactured in the same manner as in Examples 1A to 7A, and then using the guide cylinders two endoscopes as shown in FIG. 6 were manufactured in each Example.

Comparative Examples 1B to 5B

In each of Comparative Examples 1B to 5B, two guide cylinders were manufactured in the same manner as in Comparative Examples 1A to 5A, and then using the guide cylinders two endoscopes as shown in FIG. 6 were manufactured in each Comparative Example.

Comparative Example 6B

Two guide cylinders were manufactured in the same manner as in Example 1A excepting that as the brazing material a filler wire (welding wire) having the diameter of 0.4 mm and made of an alloy composed of 63 wt % of Pb and 38 wt % of Sn was used. Then, using the guide cylinders, two endoscopes as shown in FIG. 6 were manufactured.

In accordance with the following conditions, each of the endoscopes manufactured in Examples 1B to 7B and Comparative Examples 1B to 6B was subjected to sterilization treatment (disinfection treatment). Then, bending operation was carried out in each endoscope to check changes in the required force for being the flexible tube thereof, and its result was evaluated in accordance with the following four criteria A to D.

A: No change was confirmed before and after the sterilization treatment.

B: The required force was slightly increased after the sterilization treatment.

C: The required force was increased after the sterilization treatment so that the operation of the endoscope was somewhat difficult.

D: The required force was evidently increased after the sterilization treatment so that the operation of the endoscope was considerably difficult.

The sterilization treatment (disinfection treatment) was carried out as follows using the following chemicals.

Each endoscope was being immersed in a 0.3 wt % peracetic acid solution at a temperature of 20° C. for seven days. In addition, each endoscope was also being immersed in a solution of effecting chloride concentration of 50 ppm (acidic electrolyte solution) at a temperature of 20° C. for seven days.

The results of the test are shown in Table 1.

TABLE 1

| | Joining material (Compounding ratio: wt %) | Treatment conditions at heat treatment | Treatment conditions at brazing | Evaluation results | |
|---|---|---|---|---|---|
| | | | | Peracetic acid solution | Acidic electrolyte solution |
| Example 1B | Au:Ni = 82:18 | Pure hydrogen atmosphere 1130° C. × 20 minutes | Pure hydrogen atmosphere 1130° C. × 20 minutes | A | A |
| Example 2B | Au:Ni = 82:18 | Vacuum 1130° C. × 20 minutes | Pure hydrogen atmosphere 1130° C. × 20 minutes | A | A |
| Example 3B | Au:Ni = 82:18 | Pure hydrogen atmosphere 1130° C. × 20 minutes | Vacuum 1130° C. × 20 minutes | A | A |
| Example 4B | Au:Ni = 82:18 | Pure hydrogen atmosphere 1130° C. × 20 minutes | Atmospheric condition 1130° C. × 20 minutes | B | B |
| Example 5B | Au:Cu = 82:18 | Pure hydrogen atmosphere 1130° C. × 20 minutes | Pure hydrogen atmosphere 1130° C. × 20 minutes | A | A |
| Example 6B | Au = 100 | Pure hydrogen atmosphere 1130° C. × 20 minutes | Pure hydrogen atmosphere 1130° C. × 20 minutes | A | A |
| Example 7B | Au:Ag:Cu = 75:12.5:12.5 | Pure hydrogen atmosphere 1130° C. × 20 minutes | Pure hydrogen atmosphere 1130° C. × 20 minutes | A | A |
| Comparative Example 1B | Au:Ni = 82:18 | —* | Pure hydrogen atmosphere 1130° C. × 20 minutes | D | D |
| Comparative Example 2B | Au:Ni = 82:18 | Pure hydrogen atmosphere 1000° C. × 20 minutes | Pure hydrogen atmosphere 1130° C. × 20 minutes | C | C |
| Comparative Example 3B | Au:Ni = 82:18 | Pure hydrogen atmosphere 1250° C. × 20 minutes | Pure hydrogen atmosphere 1130° C. × 20 minutes | C | C |

TABLE 1-continued

|  | Joining material (Compounding ratio: wt %) | Treatment conditions at heat treatment | Treatment conditions at brazing | Evaluation results | |
|---|---|---|---|---|---|
|  |  |  |  | Peracetic acid solution | Acidic electrolyte solution |
| Comparative Example 4B | Au:Ni = 82:18 | Atmosphere 1130° C. × 20 minutes | Pure hydrogen atmosphere 1130° C. × 20 minutes | D | D |
| Comparative Example 5B | Au:Ag:Cu = 75:12.5:12.5 | —* | Pure hydrogen atmosphere 1130° C. × 20 minutes | D | D |
| Comparative Example 6B | Pb:Sn = 62:38 | Pure hydrogen atmosphere 1130° C. × 20 minutes | Pure hydrogen atmosphere 1130° C. × 20 minutes | D | D |

*Heat treatment was omitted

As shown in Table 1, all of the endoscopes of Examples of the present invention could be used without any trouble even after the completion of the test, and therefore it has been confirmed that they had excellent durability.

On the other hand, in each of the endoscopes of Comparative Examples, the required force for bending the flexible tube was increased, and therefore it has been confirmed that they had poor durability. This is supposed to result from the following cause. Namely, in each of Comparative Examples 1B to 5B, the joint portion was not sufficiently brazed or joined by the brazing material, and in Comparative Example 6B, the brazing material itself had poor chemical resistance, so that the chemical solution entered the inside of each endoscope whereby the lubricant changed its nature and deteriorated. This is believed to be the main factor for the defects of Comparative Examples.

As described above, the brazing method of the present invention makes it possible to join or braze metal components made of stainless steel for use in medical equipment with a brazing material having excellent chemical resistance and corrosion resistance as compared with the various solders conventionally used. Therefore, the present invention can be preferably applied to a joint of metal components which are required to have chemical resistance in addition to the conventional joint in which the metal components are soldered with the various solders.

Finally, it is to be understood that many changes and additions may be made to the embodiment described above without departing from the scope and spirit of the invention as defined in the following claims.

Further, it is also to be understood that the present disclosure relates to subject matter contained in Japanese Patent Applications No. 2003-299055 filed on Aug. 22, 2003 and No. 2004-219270 filed on Jul. 27, 2004 which are expressly incorporated herein by reference in their entireties.

What is claimed is:

1. A method for brazing two or more of metal components made of stainless steel for use in medical equipment, in which one component is joined to other component using a brazing material containing Au of which amount is 62.5 wt % or higher, the method comprising:

subjecting the components to a heat treatment at a temperature of 1,050 to 1,200° C. in a hydrogen containing atmosphere or in a vacuum;

thereafter bringing one of the components close to the other component so as to form a gap therebetween; and supplying the brazing material containing Au of which amount is 62.5 wt % or higher in a molten state into the gap to join the metal components together.

2. The method as claimed in claim 1, wherein the heat treatment is in a hydrogen containing atmosphere, and a dew point of the hydrogen containing atmosphere is −60° C. or lower.

3. A method for brazing two or more of metal components made of stainless steel for use in medical equipment, at least one of the metal components being a hollow member, in which one component is joined to other component using a brazing material containing Au of which amount is 62.5 wt % or higher, the method comprising:

subjecting the components to a heat treatment at a temperature of 1,050 to 1,200° C. in a hydrogen containing atmosphere or in a vacuum;

thereafter a part of one component is inserted into the other component so as to form a gap therebetween; and supplying the brazing material containing Au of which amount is 62.5 wt % or higher in a molten state into the gap to join the metal components together.

4. The method as claimed in claim 3, wherein each of the metal components is a hollow member having an internal cavity, in which the gap is formed by inserting a part of one component into the internal cavity of the other component.

5. The method as claimed in claim 1, wherein the average width of the gap is in the range of 0.02 to 0.25 mm.

6. The method as claimed in claim 1, wherein the method further comprises, prior to the supplying the brazing material in a molten state into the gap, temporarily fixing the components by welding a part of the one component to a part of the other component by laser welding.

7. The method as claimed in claim 1, wherein the method further comprises, prior to supplying the brazing material in a molten state into the gap, applying the brazing material along an opening of the gap, in which the brazing material is molten by heating the brazing material thereby supplying the brazing material in a molten state into the gap.

8. The method as claimed in claim 7, wherein in the supplying the brazing material in a molten state includes heating at a temperature is in the range of 1,050 to 1,200° C.

9. The method as claimed in claim 1, wherein the supplying the brazen material in a molten state is performed in a hydrogen containing atmosphere or in a vacuum.

10. The method as claimed in claim 1, wherein the bringing one of the components close to the other component so as to form a gap therebetween includes bringing the metal components close to each other so that a surface of one metal component faces a surface of the other metal component, and forming at least one protrusion on at least one of the surfaces of the metal components so as to protrude toward the other surface.

11. The method as claimed in claim 10, wherein the protrusion is formed by overlying welding.

12. The method as claimed in claim 10, wherein the forming the protrusion is carried out prior to the subjecting the components to a heat treatment.

13. The method as claimed in claim 1, wherein the brazing material is at least one selected from pure gold, Au—Ni based alloys, Au—Cu based alloys and Au—Ag—Cu based alloys.

* * * * *